United States Patent
Cheon et al.

(10) Patent No.: US 8,778,411 B2
(45) Date of Patent: Jul. 15, 2014

(54) HEAT GENERATING NANOMATERIALS

(75) Inventors: Jin Woo Cheon, Seoul (KR); Jung Tak Jang, Seoul (KR)

(73) Assignee: Industry-Academic Cooperation Foundation, Yonsei University, Seoul (KR)

(*) Notice: Subject to any disclaimer, the term of this patent is extended or adjusted under 35 U.S.C. 154(b) by 263 days.

(21) Appl. No.: 12/993,293

(22) PCT Filed: May 20, 2009

(86) PCT No.: PCT/KR2009/002661
§ 371 (c)(1),
(2), (4) Date: Feb. 10, 2011

(87) PCT Pub. No.: WO2009/142438
PCT Pub. Date: Nov. 26, 2009

(65) Prior Publication Data
US 2011/0151019 A1 Jun. 23, 2011

(30) Foreign Application Priority Data
May 20, 2008 (KR) .................... 10-2008-0046589

(51) Int. Cl.
 A61K 33/24 (2006.01)
 A61K 33/26 (2006.01)
 A61K 33/32 (2006.01)
 A61B 5/055 (2006.01)
(52) U.S. Cl.
 USPC ............ 424/646; 424/617; 424/639; 424/9.3
(58) Field of Classification Search
 None
 See application file for complete search history.

(56) References Cited

U.S. PATENT DOCUMENTS
2005/0249817 A1* 11/2005 Haik et al. .................... 424/617

FOREIGN PATENT DOCUMENTS
JP 09-324957 A 12/1997
JP 2004-244484 A 9/2004

OTHER PUBLICATIONS

Masala et al. "Preparation of magnetic spinel ferrite core/shell nanoparticles: Soft ferrites on hard ferrites and vice versa" Solid State Sciences, vol. 8, p. 1015-1022 (2006).*
International Search Report from International Application No. PCT/KR2009/002661, dated Dec. 22, 2009 (date of completion of search) and Jan. 4, 2010 (date of mailing of report).

* cited by examiner

Primary Examiner — Abigail Fisher
Assistant Examiner — Daniel L Branson
(74) Attorney, Agent, or Firm — Clark & Elbing LLP

(57) ABSTRACT

The present invention relates to a heat-generating composition, comprising a hetero-structure nanomaterial which comprises (a) a first material comprising at least one component selected from the group consisting of a metal, a metal chalcogen, a metal pnicogen, an alloy and a multi-component hybrid structure thereof; and (b) a second material comprising at least one component selected from the group consisting of metal, metal chalcogen, metal pnicogen, alloy and the multi-component hybrid structure thereof; wherein the first material is enclosed in the second material; wherein at least one of the first material and the second material comprise a magnetic material. The specific loss power of the present nanomaterial is much higher than that of conventional nanomaterials (e.g., 40-fold higher than commercially accessible Feridex) and may be controlled by changing compositions or ratios of the first material and/or the second material. The heat-generating nanomaterial of the present invention may be used in a variety of application fields, for example cancer hyperthermia.

6 Claims, 7 Drawing Sheets

HEAT GENERATING NANOMATERIALS

CROSS-REFERENCE TO RELATED APPLICATIONS

This application is the U.S. national stage filing under 35 U.S.C. §371 of international application PCT/KR2009/002661, filed May 20, 2009, which claims benefit of Korean Patent Application 10-2008-0046589, filed May 20, 2008.

BACKGROUND OF THE INVENTION

1. Field of the Invention

The present invention relates to heat-generating nanomaterials having a hetero-structure.

2. Description of the Related Art

Nanomaterials have new physiochemical characteristics different from bulk materials due to their minute size. The intensive researches for the nanomaterials permit nanomaterials to be precisely controlled in their composition and shape as well as the size, enabling that the physiochemical properties in a nano-region can be controlled like those in a bulk-region. Using these novel properties, the nanomaterials has been currently utilized in a variety of applications such as catalysts for chemical reactions, fabrication of next generation nanodevices, development of new sources of energy, and cancer diagnosis and therapy in combination with a biomedical science (nano-medicine).

Of them, magnetic nanomaterials generate heat under a magnetic field of high frequency by (a) Brownian relaxation caused by rotation of nanomaterials dispersed in a liquid solution and (b) Neel relaxation caused from energy barrier of internal spin of nanomaterials ($E=KV$, where K is the anisotropy constant and V is the volume of the nanomaterial) due to their unique magnetic property (*J. Mater. Chem.*, 2004, 14, 2161-2175). Using heat generated thus, the magnetic nanomaterials may be applied to a multitude of heat-generating devices or technologies. Specially, in medical area, heat generated from the magnetic materials under a magnetic field of high frequency has been used in hyperthermia for various diseases and disorders such as cancer.

Heat generated by magnetic nanomaterials may be quantitated by a specific loss power (SLP). As referred to R. E. Rosensweig *J. Magn. Magn. Mater.* 2002, 252, 370-374, the value of specific loss power was determined according to various factors of materials, in particular a spin anisotropy and a saturation magnetism ($M_s$).

In this context, various research groups have made intensive studies to develop nanomaterials having higher specific loss power. Up to date, the applicable fields of heat generation using nanomaterials are as follows:

U.S. Pat. No. 7,282,479 discloses a hyperthermia agent for malignant tumors comprising the magnetic fine particles such as ferrite, magnetite or permalloy.

US Pat. Appln. No. 2005-0090732 discloses a targeted thermotherapy using an iron oxide.

U.S. Pat. No. 6,541,039 discloses a hyperthermia method using an iron oxide coated by a silica or polymer.

WO2006/102307 discloses a method for hyperthermia using the magnetic nanoparticle in which a core coated with a noble metal is surrounded by other organic shell, followed by packing with an antibody or a fluorescent material.

However, the nanoparticles disclosed in U.S. Pat. No. 7,282,479 and US Pat. Appln. No. 2005-0090732 are related to a cancer therapy using magnetic nanoparticles with a single structure. In addition, it is one of the purposes of the above-mentioned patents to develop a therapeutic agent for target a cancer by attaching targeting substances to conventional magnetic materials, instead of increasing the specific loss power of magnetic nanoparticles.

In U.S. Pat. No. 6,541,039 and WO2006/102307, the heat-generating nanoparticle coated with multiple shells is provided but the components of shells are unlikely to contribute to enhancement of the specific loss power of magnetic nanoparticles.

The main reason why there is limitations on the increase in the specific loss power of nanoparticles is because most of researches on physiochemical characteristics of nanomaterials is focused on the controlling their size, shape and/or composition of simple structural nanomaterials. Therefore, these nanomaterials with a simple structure have serious limitations in their function or stability. As an alternative to overcome the drawbacks, the hetero-structure nanocomplex has been provided to have a high- and multi-functionality remarkably better than simple structural nanomaterials. For example, CdSe@ZnS (*Nano Lett.* 2001, 1, 207-211) or CdSe@CdS (*J. Am. Chem. Soc.* 1997, 119, 7019-7029) nanocomplex has an increased optical property and stability compared to simple structural nanomaterials. In addition, FePt@Fe$_3$O$_4$ (*Nano Lett.* 2004, 4, 187-190) nanocomplex has novel magnetic properties. As such, the hetero-structure nanocomplex exhibits new optical, magnetic and chemical characteristics due to interactions between its components, not observed in simple structural nanomaterials.

As described above, a number of studies for hyperthermia using magnetic materials have been attempted; however the magnetic nanomaterials used so far had some limitations in the increase of the value of specific loss power due to their restricted physiochemical characteristics. Accordingly, the present invention may be suggested as a new alternative since a hetero-structure nanomaterial in the present invention shows a dramatic heat-generating effect.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventors have made intensive researches to develop a novel nanomaterial having a remarked specific loss power to overcome shortcomings in which conventional magnetic nanomaterials with a single composition have low heat-generation coefficient under a magnetic field of high frequency. As results, we have discovered that nanomaterials prepared to have a hetero-structure enable to successfully overcome problems associated with simple-structure nanomaterials having restricted physiochemical characteristics, resulting in significant enhancement of physiochemical characteristics of nanomaterials.

The present inventors have discovered that the heat generation of nanomaterials is dramatically increased (e.g. 40-fold higher than commercially accessible Feridex) by our novel fabrication approach in which nanomaterials are provided with a hetero-structure composed of a first material and a second material and a magnetic material is introduced into at least one of the first material and the second material. The considerable increase in specific loss power is ascribed to increase in both spin anisotropy and saturation magnetism ($M_s$) of nanomaterials due to spin interactions between the first material and the second material.

Accordingly, it is an object of this invention to provide a heat-generating composition comprising a hetero-structure nanomaterial with remarkably enhanced specific loss power.

It is another object of this invention to provide a composition for hyperthermia.

Other objects and advantages of the present invention will become apparent from the following detailed description together with the appended claims and drawings.

DETAILED DESCRIPTION OF THE INVENTION

Figure 1:
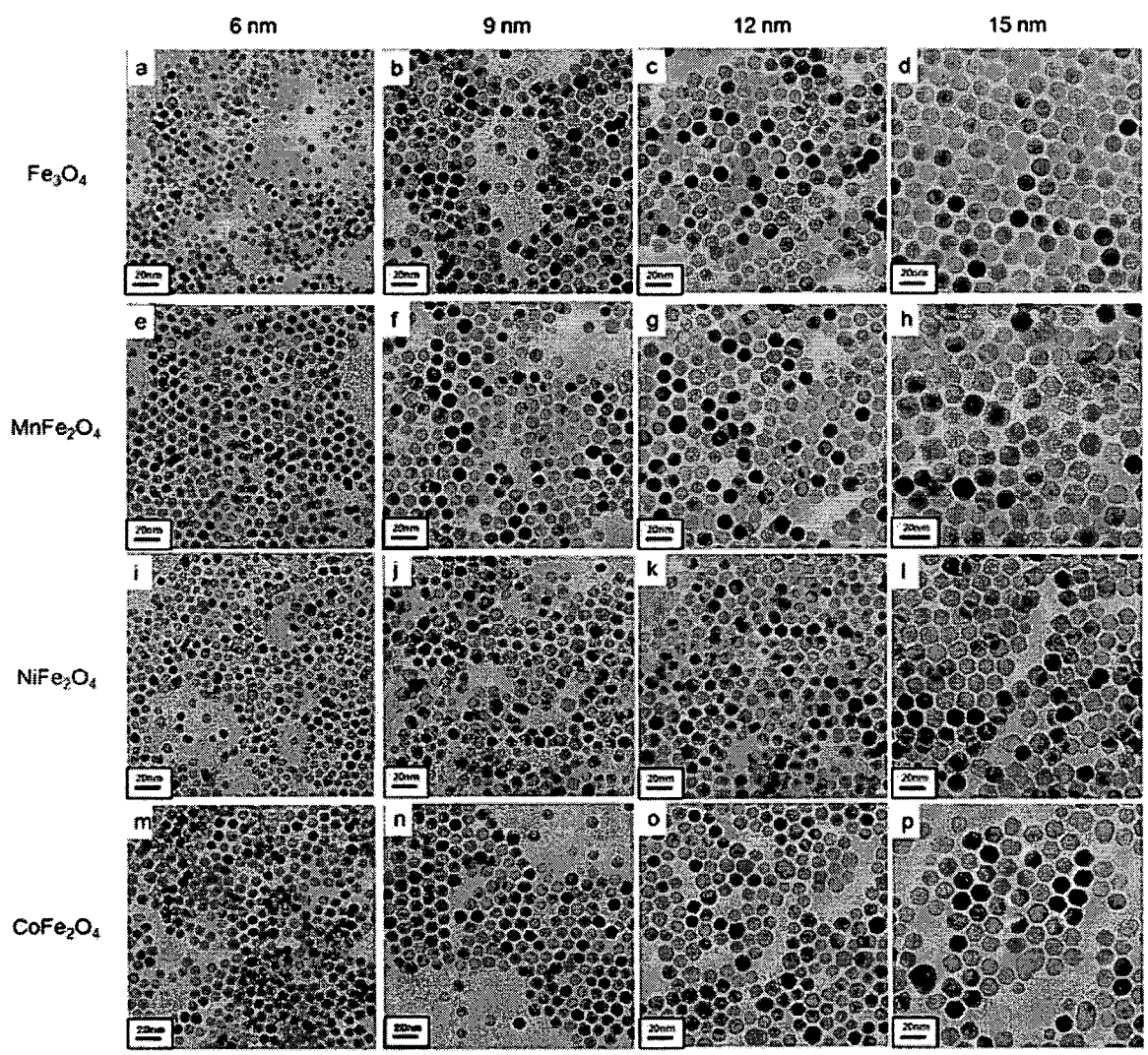
FIG. 1 shows TEM (transmission electron microscopy) images of ferrite nanomaterials synthesized. The images of $Fe_3O_4$, $MnFe_2O_4$, $NiFe_2O_4$ and $CoFe_2O_4$ are represented in panels a-d, e-h, i-l and m-p, respectively. Each $Fe_3O_4$, $MnFe_2O_4$, $NiFe_2O_4$ and $CoFe_2O_4$ with a size of 6, 9, 12 and 15 nm has a homogeneous size distribution ($\delta < 10\%$).

In one aspect of this invention, there is provided a heat-generating composition, comprising a hetero-structure nanomaterial which comprises (a) a first material comprising at least one component selected from the group consisting of a metal, a metal chalcogen (Group 16 element), a metal pnicogen (Group 15 element), an alloy and a multi-component hybrid structure thereof; and (b) a second material comprising at least one component selected from the group consisting of metal, metal chalcogen, metal pnicogen, alloy and the multi-component hybrid structure thereof; wherein the first material is enclosed in the second material; wherein at least one of the first material and the second material comprise a magnetic material.

The present inventors have discovered that the heat generation of the present nanomaterial is dramatically increased (e.g. 40-fold higher than commercially accessible Feridex) by our novel fabrication approach in which nanomaterials are provided with a hetero-structure composed of a first material and a second material and a magnetic material is introduced into at least one of the first material and the second material.

It is one of the most prominent features of the present invention that the nanomaterial for heat generation is prepared to have the hetero-structure including a single or multi-component magnetic nanomaterial. The preparation strategy is suggested by our novel findings that the heat generation from hetero-structure nanomaterials is much higher than those from simple-structure magnetic nanomaterials.

The first and second material all include metal, metal chalcogen, metal pnicogen, alloy and the multi-component hybrid structure having the same and at least one of the first or second material include a magnetic material.

The metal involved in the first or second material includes transition metal elements, Lanthanide metal elements or Actinide metal elements. More preferably, the metal nanomaterial is selected from the group consisting of transition metal elements selected from the group consisting of Co, Mn, Fe and Ni, or Lanthanide metal elements and Actinide metal elements selected from the group consisting of Nd, Gd, Tb, Dy, Ho, Er and Sm, or the multi-component hybrid structure having the same.

The metal chalcogen involved in the first or second material includes $M^a_xA_y$, -$M^a_xM^b_yA_z$ ($M^a$ and $M^b$ independently represent one or more elements selected from the group consisting of Group 1 metal elements, Group 2 metal elements, transition metal elements, metal or metalloid elements of Groups 13-15 elements, Lanthanide metal elements and Actinide metal elements; A is selected from O, S, Se, Te or Po; $0 \leq x \leq 32$, $0 \leq y \leq 32$, $0 < z \leq 8$) or the multi-component hybrid structure thereof.

More preferably, the metal chalcogen includes a $M^a_xA_y$ or a $M^a_xM^b_yA_z$ nanomaterial ($M^a$=one or more elements selected from transition metal elements selected from the group consisting of Ba, Cr, Mn, Fe, Co, Ni, Cu, Zn, Nb, Mo, Zr, Te, W, Pd, Ag, Pt and Au, Groups 13-15 elements selected from the group consisting of Ga, In, Sn, Pb and Bi, or Lanthanide metal elements and Actinide metal elements selected from the group consisting of Gd, Tb, Dy, Ho, Er, Sm and Nd; $M^b$=one or more elements selected from Group 1 metal elements, Group 2 metal elements, transition metal elements, metal or metalloid elements of Groups 13-15 elements, Lanthanide metal elements and Actinide metal elements; A is selected from O, S, Se, Te or Po; $0 \leq x \leq 32$, $0 \leq y \leq 32$, $0 < z \leq 8$) or the multi-component hybrid structure thereof.

Still more preferably, the metal chalcogen includes $M^a_xO_z$, $M^a_xM^b_yO_z$ [$M^a$=one or more elements selected from transition metal elements selected from the group consisting of Ba, Cr, Mn, Fe, Co, Ni, Cu, Zn, Nb, Mo, Zr, Te, W, Pd, Ag, Pt and Au, and Lanthanide metal elements and Actinide metal elements selected from the group consisting of Gd, Tb, Dy, Ho, Er, Sm and Nd; $M^b$=one or more elements selected from the group consisting of Group 1 metal elements (Li or Na), Group 2 metal elements (Be, Ca, Mg, Sr, Ba or Ra), Group 13 elements (Ga or In), Group 14 elements (Si or Ge), Group 15 elements (As, Sb or Bi), Group 16 elements (S, Se or Te), transition metal elements (Sr, Ti, V, Cu, Y, Zr, Nb, Mo, Tc, Ru, Rh, Pd, Ag, Cd, Hf, Ta, W, Re, Os, Ir, Pt, Au or Hg), and Lanthanide metal elements and Actinide metal elements (La, Ce, Pr, Nd, Pm, Sm, Eu, Gd, Tb, Dy, Ho, Er, Tm or Yb); $0 \leq x \leq 16$, $0 \leq y \leq 16$, $0 < z \leq 8$] or the multi-component hybrid structure thereof.

Most preferably, the metal chalcogen includes $M^h_xFe_yO_z$ ($M^h$=one or more elements selected from transition metal elements selected from the group consisting of Ba, Zn, Mn, Fe, Co and Ni; $0 < x \leq 8$, $0 \leq y \leq 8$, $0 \leq z \leq 8$), $Zn_wM^i_xFe_yO_z$ ($M^i$=one or more elements selected from the group consisting of Group 1 metal elements, Group 2 metal elements, Groups 13 metal elements, transition metal elements, Lanthanide metal elements and Actinide metal elements; $0<w\leq8$, $0<x\leq8$, $0\leq y\leq8$, $0\leq z\leq8$), or $M^a{}_xO_y$ ($M^a$=one or more elements selected from transition metal elements selected from the group consisting of Ba, Zn, Mn, Fe, Co and Ni, and Lanthanide metal elements selected from the group consisting of Gd, Tb, Dy, Ho, Er and Nd; $0<x\leq16$, $0\leq y\leq8$).

Preferably, the metal pnicogen includes $M^c{}_xA_y$, $M^c{}_xM^d{}_yA_z$ ($M^c$ and $M^d$ independently represent one or more elements selected from the group consisting of Group 1 metal elements, Group 2 metal elements, transition metal elements; metal and metalloid elements of Groups 13-14 elements, Lanthanide metal elements and Actinide metal elements; A is selected from N, P, As, Sb or Bi; $0\leq x\leq40$, $0\leq y\leq40$, $0<z\leq8$) or the multi-component hybrid structure thereof.

More preferably, the metal pnicogen includes $M^c{}_xA_y$, $M^c{}_xM^d{}_yA_z$ ($M^c$=one or more elements selected from transition metal elements selected from the group consisting of Ba, Cr, Mn, Fe, Co, Ni, Cu, Zn, Cd, Hg, Nb, Mo, Zr, W, Pd, Ag, Pt and Au, Groups 13-14 elements selected from the group consisting of Ga, In, Sn and Pb, or Lanthanide metal elements and Actinide metal elements selected from the group consisting of Gd, Tb, Dy, Ho, Er, Sm and Nd; $M^d$=one or more elements selected from the group consisting of Group 1 metal elements, Group 2 metal elements, transition metal elements, metal and metalloid elements of Groups 13-14 elements, Lanthanide metal elements and Actinide metal elements; A is selected from N, P, As, Sb or Bi; $0\leq x\leq40$, $0\leq y\leq40$, $0<z\leq8$) or the multi-component hybrid structure thereof.

The alloy involved in the first or second material includes preferably $M^e{}_xM^f{}_y$, $M^e{}_xM^f{}_yM^g{}_z$ ($M^e$=one or more elements selected from transition metal elements selected from the group consisting of Ba, Cr, Mn, Fe, Co, Ni, Cu, Zn, Nb, Mo, Zr, Te, W, Pd, Ag, Pt and Au, and Lanthanide metal elements and Actinide metal elements selected from the group consisting of Gd, Tb, Dy, Ho, Er, Sm and Nd; $M^f$ and $M^g$ independently represent one or more elements selected from the group consisting of Group 1 metal elements, Group 2 metal elements, Group 13 elements, Group 14 elements, Group 15 elements, Group 16 elements, transition metal elements, Lanthanide metal elements and Actinide metal elements; $0<x\leq20$, $0<y\leq20$, $0\leq z\leq20$), and more preferably, $M^e{}_xM^f{}_y$ or $M^e{}_xM^f{}_yM^g{}_z$ ($M^e$, $M^f$ or $M^g$ independently represents one or more element selected from the group consisting of Co, Fe, Mn, Ni, Mo, Si, Al, Cu, Pt, Sm, B, Bi, Cu, Sn, Sb, Ga, Ge, Pd, In, Au, Ag and Y; $0<x\leq20$, $0<y\leq20$, $0\leq z\leq20$).

According to a preferable embodiment, the first material or the second material includes:

(a) the metal, M (M=Ba, Cr, Mn, Fe, Co, Zn, Nb, Mo, Zr, Te, W, Pd, Gd, Tb, Dy, Ho, Er, Sm or Nd);

(b) the metal chalcogen, $M^h{}_xFe_yO_z$ ($M^h$=one or more elements selected from transition metal elements selected from the group consisting of Ba, Zn, Mn, Fe, Co and Ni; $0<x\leq8$, $0\leq y\leq8$, $0\leq z\leq8$), $Zn_xFe_yO_z$ ($0<x\leq8$, $0<y\leq8$, $0<z\leq8$), $Zn_wM^i{}_xFe_yO_z$ ($M^i$=one or more elements selected from the group consisting of Group 1 metal elements, Group 2 metal elements, Group 13 elements, transition metal elements, Lanthanide metal elements and Actinide metal elements; $0<w\leq8$, $0\leq x\leq8$, $0<y\leq8$, $0<z\leq8$), or $M^a{}_xO_y$ ($M^a$=one or more selected from the group consisting of transition metal elements selected from the group consisting of Ba, Zn, Mn, Fe, Co and Ni, and Lanthanide metal elements selected from the group consisting of Gd, Tb, Dy, Ho and Er; $0<x\leq16$, $0\leq y\leq8$);

(c) the alloy, $M^e{}_xM^f{}_y$ or $M^e{}_xM^f{}_yM^g{}_z$ ($M^e$, $M^f$ and $M^g$ independently represent one or more elements selected from the group consisting of Co, Fe, Mn, Ni, Mo, Si, Al, Cu, Pt, Sm, B, Bi, Cu, Sn, Sb, Ga, Ge, Pd, In, Au, Ag and Y; $0<x\leq20$, $0\leq y\leq20$, $0\leq z\leq20$);

(d) $YCO_5$, MnBi or $BaFe_{12}O_{19}$; or (e) the multi-component hybrid structure thereof.

Still more preferably, the first material and the second material independently is at least one selected from $M^h{}_xFe_yO_z$ ($M^h$=one or more elements selected from the group consisting of Ba, Zn, Mn, Fe, Co and Ni; ($0<x\leq8$, $0\leq y\leq8$, $0\leq z\leq8$), $Zn_xFe_yO_z$ ($0<x\leq8$, $0<y\leq8$, $0<z\leq8$), $Zn_wM^i{}_xFe_yO_z$ ($M^i$=one or more elements selected from the group consisting of Group 1 metal elements, Group 2 metal elements, Group 13 elements, transition metal elements, Lanthanide metal elements and Actinide metal elements; $0<w\leq8$, $0\leq x\leq8$, $0<y\leq8$, $0<z\leq8$), $YCO_5$, MnBi or $BaFe_{12}O_{19}$.

According to a preferable embodiment, the first material and/or the second material include one or more magnetic materials. In this case, the magnetic materials of the first or second material are preferably different to each other.

According to a preferable embodiment, the first material and the second material include $M^h{}_xFe_yO_z$ ($M^h$=one or more elements selected from the group consisting of Ba, Zn, Mn, Fe, Co and Ni; $0\leq x\leq16$, $0<y\leq16$, $0<z\leq8$), $Zn_xFe_yO_z$ ($0<x\leq8$, $0<y\leq8$, $0<z\leq8$), $Zn_wM^i{}_xFe_yO_z$ ($M^i$=one or more elements selected from the group consisting of Group 1 metal elements, Group 2 metal elements, Group 13 elements, transition metal elements, Lanthanide metal elements and Actinide metal elements; $0<w\leq16$, $0\leq x\leq16$, $0<y\leq16$, $0<z=8$), $YCO_5$, MnBi or $BaFe_{12}O_{19}$. It is preferable in this case that the magnetic materials of the first or second material are different to each other.

More preferably, any one of the first material and the second material includes $YCO_5$, MnBi, $BaFe_{12}O_{19}$ or $CoFe_2O_4$.

The term "hetero-structure" refers to a structure in which two or more materials having distinctly different characteristics are combined to each other. The hetero-structure nanomaterial of the present invention may include any one of various hetero-structures known to those ordinarily skilled in the art. Preferably, the nanomaterial of the present invention includes (i) a zero-dimensional structure selected from the group consisting of a core-shell and a multi-core shell structure; (ii) a one-dimensional structure selected from the group consisting of a barcode, a core-shell coaxial rod and a multi-core shell coaxial rod structure; (iii) a two-dimensional structure comprising a multi-component sheet structure; or (iv) a three-dimensional structure selected from the group consisting of a dumbbell and a multi-pod structure.

The heat-generating nanomaterial of this invention has a size in a range of preferably 1-1000 nm and more preferably 2-500 nm.

The hetero-structure nanomaterial of this invention may control the specific loss power by changing compositions or ratios of the first material or the second material. For example, the specific loss power may be controlled in a core-shell structure by manipulating thickness or layer of shell.

According to a preferable embodiment, the nanomaterial of this invention has a specific loss power value in a range of 2-20000 W/g, more preferably 50-10000 W/g, much more preferably 100-5000 W/g and most preferably 200-5000 W/g.

According to a preferable embodiment, the hetero-structure nanomaterial of this invention may be attached with a bioactive material (example: an antibody, a protein, an antigen, a peptide, a nucleic acid, an enzyme, a cell, etc.) or a chemically active material (example: a monomer, a polymer, an inorganic material, a fluorescent material, a drug, etc.).

The bioactive material includes an antibody, a protein, an antigen, a peptide, a nucleic acid, an enzyme or a cell. Preferably, it includes, but not limited to, a protein, a peptide, DNA, RNA, an antigen, hapten, avidin, streptavidin, neutravidin, protein A, protein G, lectin, selectin, hormone, interleukin, interferon, growth factor, tumor necrosis factor, endotoxin, lymphotoxin, urokinase, streptokinase, tissue plasminogen activator, a biological active enzyme such as hydrolase, oxido-reductase, lyase, isomerase and synthetase, enzyme cofactor or enzyme inhibitor.

The chemically active material includes several functional monomers, polymers, inorganic materials, fluorescent organic materials or drugs.

Exemplified monomer described hereinabove includes, but not limited to, a drug containing anti-cancer drug, antibiotics, Vitamin and folic acid, a fatty acid, a steroid, a hormone, a purine, a pyrimidine, monosaccharides and disaccharides. The side chain of the above-described monomer includes one or more functional groups selected from the group consisting of —COOH, —NH$_2$, —SH, —SS—, —CONH$_2$, —PO$_3$H, —OPO$_4$H$_2$, —PO$_2$(OR$^1$)(OR$^2$) (R$^1$, R$^2$=C$_s$H$_t$N$_u$O$_w$S$_x$P$_y$X$_z$, X=—F, —Cl, —Br or —I, 0≤s≤20, 0≤t≤2(s+u)+1, 0≤u≤2s, 0≤w≤2s, 0≤x≤2s, 0≤y≤2s, 0≤z=2s), —SO$_3$H, —OSO$_3$H, —NO$_2$, —CHO, —COSH, —COX, —COOCO—, —CORCO—(R=C$_l$H$_m$, 0≤l≤3, 0≤m≤2l+1), —COOR, —CN, —N$_3$, —N$_2$, —NROH(R=C$_s$H$_t$N$_u$O$_w$S$_x$P$_y$X$_z$, X=–F, —Cl, —Br or —I, 0≤s≤20, 0≤t≤2(s+u)+1, 0≤u≤2s, 0≤w≤2s, 0≤x≤2s, 0≤y≤2s, 0≤z≤2s), —NR$^1$NR$^2$R$^3$ (R$^1$, R$^2$, R$^3$=C$_s$H$_t$N$_u$O$_w$S$_x$P$_y$X$_z$, X=—F, —Cl, —Br or —I, 0≤s≤20, 0≤t≤2(s+u)+1, 0≤u≤2s, 0≤w≤2s, 0≤x≤2s, 0≤y≤2s, 0≤z≤2s), —CONHNR$^1$R$^2$ (R$^1$, R$^2$=C$_s$H$_t$N$_u$O$_w$S$_x$P$_y$, X=—F, —Cl, —Br or —I, 0≤s≤20, 0≤t≤2(s+u)+1, 0≤u≤2s, 0≤w≤2s, 0≤x≤2s, 0≤y=2s, 0≤z≤2s), —NR$^1$R$^2$R$^3$X' (R$^1$, R$^2$, R$^3$=C$_s$H$_t$N$_u$O$_w$S$_x$P$_y$X$_z$, X=—F, —Cl, —Br or —I, X'=F$^-$, Cl$^-$, Br$^-$ or I$^-$, 0≤s≤20, 0≤t≤2(s+u)+1, 0≤u≤2s, 0≤w≤2s, 0≤x≤2s, 0≤y≤2s, 0≤z≤2s), —OH, —SCOCH$_3$, —F, —Cl, —Br, —I, —SCN, —NCO, —OCN, -epoxy group, —HN—NH$_2$, —HC=CH— and —C≡CH—.

The example of the above-described chemical polymer includes dextran, carbodextran, polysaccharide, cyclodextran, pullulan, cellulose, starch, glycogen, monosaccharides, disaccharides and oligosaccharides, polyphosphagen, polylactide, polylactide-co-glycolide, polycaprolactone, polyanhydride, polymaleic acid and a derivative of polymaleic acid, polyalkylcyanoacrylate, polyhydroxybutylate, polycarbonate, polyorthoester, polyethylene glycol, poly-L-lysine, polyglycolide, polymethyl methacrylate, polymethylether methacrylate and polyvinylpyrrolidone, but not limited to.

Exemplified chemical inorganic material described above includes a metal oxide, a metal chalcogen compound, an inorganic ceramic material, a carbon material, a semiconductor substrate consisting of Group II/VI elements, Group, III/VI elements and Group IV elements, a metal substrate or complex thereof, and preferably, SiO$_2$, TiO$_2$, ITO, nanotube, graphite, fullerene, CdS, CdSe, CdTe, ZnO, ZnS, ZnSe, ZnTe, Si, GaAs, AlAs, Au, Pt, Ag or Cu.

The example of the above-described chemical fluorescent material includes fluorescein and its derivatives, rhodamine and its derivatives, lucifer yellow, B-phytoerythrin, 9-acrydine isothiocyanate, lucifer yellow VS, 4-acetamido-4'-isothiocyanatostilbene-2,2'-disulfonate, 7-diethylamino-3-(4'-isothiocyatophenyl)-4-methylcoumarin, succinimidylpyrenebutyrate, 4-acetoamido-4'-isothiocyanatostilbene-2, 2'-disulfonate derivatives, LC™-Red 640, LC™-Red 705, Cy5, Cy5.5, resamine, isothiocyanate, diethyltriamine pentaacetate, 1-dimethylaminonaphthyl-5-sulfonate, 1-anilino-8-naphthalene, 2-p-toluidinyl-6-naphthalene, 3-phenyl-7-isocyanatocoumarin, 9-isothiocyanatoacridine, acridine orange, N-(p-(2-benzoxazolyl)phenyl)meleimide, benzoxadiazol, stilbene and pyrene, but not limited to.

Since the nanomaterial of the present invention has very remarked heat-generation coefficient, it may be used not only in a variety of heat-generating devices but also in hyperthermia or drug release for biomedical purpose. In more detail, the heat-generating nanomaterial of the present invention may be applied to uses such as cancer treatment, pain relief, vessel treatment, bone recovery, drug activation or drug release.

As described in the Examples below, the heat-generating nanomaterial of the present invention exhibits much enhanced specific loss power. Surprisingly, the heat-generating nanomaterial of the present invention has much higher specific loss power (40-fold higher; MnFe$_2$O$_4$@CoFe$_2$O$_4$, 3034 W/g) than the commercially accessible Feridex (78 W/g). The superior specific loss power of nanomaterials of the present invention allows to kill targeted cells (e.g., cancer cells) even with a low dose.

In another aspect of this invention, there is provided a composition for hyperthermia comprising the heat-generating composition of this invention.

In still another aspect of this invention, there is provided a method for hyperthermia, which comprises administering to a subject the heat-generating composition of this invention.

Since the present composition comprises the heat-generating nanomaterial of this invention as active ingredients described above, the common descriptions between them are omitted in order to avoid undue redundancy leading to the complexity of this specification.

The composition of this invention may be provided as a pharmaceutical composition. Therefore, the composition of the present invention may be administrated together with a pharmaceutically acceptable carrier, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. Details of suitable pharmaceutically acceptable carriers and formulations can be found in *Remington's Pharmaceutical Sciences* (19th ed., 1995), which is incorporated herein by reference.

The composition according to the present invention may be parenterally administered. In the case that the contrast agent is administered parenterally, it is preferably administered by intravenous, subcutaneous, intramuscular, intraperitoneal or intralesional injection. A suitable dosage amount of the composition of the present invention may vary depending on pharmaceutical formulation methods, administration methods, the patient's age, body weight, sex, pathogenic state, diet, administration time, administration route, an excretion rate and sensitivity for a used nanomaterial. The composition of the present invention includes a therapeutically effective amount of the heat-generating composition. The term "therapeutically effective amount" refers to an amount enough to show and accomplish images of human body and is generally administered with a daily dosage of 0.0001-100 mg/kg.

According to the conventional techniques known to those skilled in the art, the pharmaceutical composition of the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

In particular, the present invention is very useful in cancer treatment. For example, the present composition may effectively induce cancer cell apoptosis in various cancer diseases such as stomach, lung, breast, ovarian, liver, bronchogenic, nasopharyngeal, laryngeal, pancreatic, bladder, colon, cervical, brain, prostatic, bone, skin, thymus, hyperthymus and ureteral carcinoma.

The composition of the present invention is administrated into a patient through suitable administration route and then is kept to stand under magnetic field of high frequency, resulting in heat generation. High frequency magnetic field of electromagnetic wave having the frequency of from 1 kHz to 10 MHz may be utilized.

The features and advantages of the present invention will be summarized as follows:

(i) the heat-generating nanomaterial of the present invention has a hetero-structure.

(ii) the heat-generating nanomaterial of the present invention exhibits greatly enhanced specific loss power (40-fold higher than commercially accessible Feridex).

(iii) the present nanomaterial may control the specific loss power by changing compositions or ratios of the first material and/or the second material.

(iv) the present nanomaterial may be used in devices for heat generation, for example cancer hyperthermia.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Preparation of Magnetic Nanomaterials Having Different Sizes and Compositions

The metal oxide nanomaterial used in Examples was produced according to the methods described in Korean Pat. No. 10-0604975 and PCT/KR2004/003088 filed by the present inventors. As precursors of nanoparticles, $MCl_2$ ($M=Mn^{2+}$, $Fe^{2+}$, $Ni^{2+}$, $Co^{2+}$, and $Zn^{2+}$) (Aldrich, USA) and $Fe(acac)_3$ (Aldrich, USA) were added to trioctylamine solvent (Aldrich, USA) containing 4 mmol oleic acid (Aldrich, USA) and 4 mmol oleylamine (Aldrich, USA) as capping molecules. The mixture was incubated at 200° C. under argon gas atmosphere and further reacted at 300° C. The synthesized nanomaterials were precipitated by excess ethanol and were again dispersed in toluene, obtaining a colloid solution. The size of synthesized nanomaterials could be feasibly manipulated depending on mole number of oleic acid and oleylamine added to the reaction. In addition, composition could be varied depending on the addition ratio of $Fe(acac)_3$ and $MCl_2$ ($M=Mn^{2+}$, $Fe^{2+}$, $Ni^{2+}$, $Co^{2+}$, and $Zn^{2+}$) as initial reactants.

Figure 2:
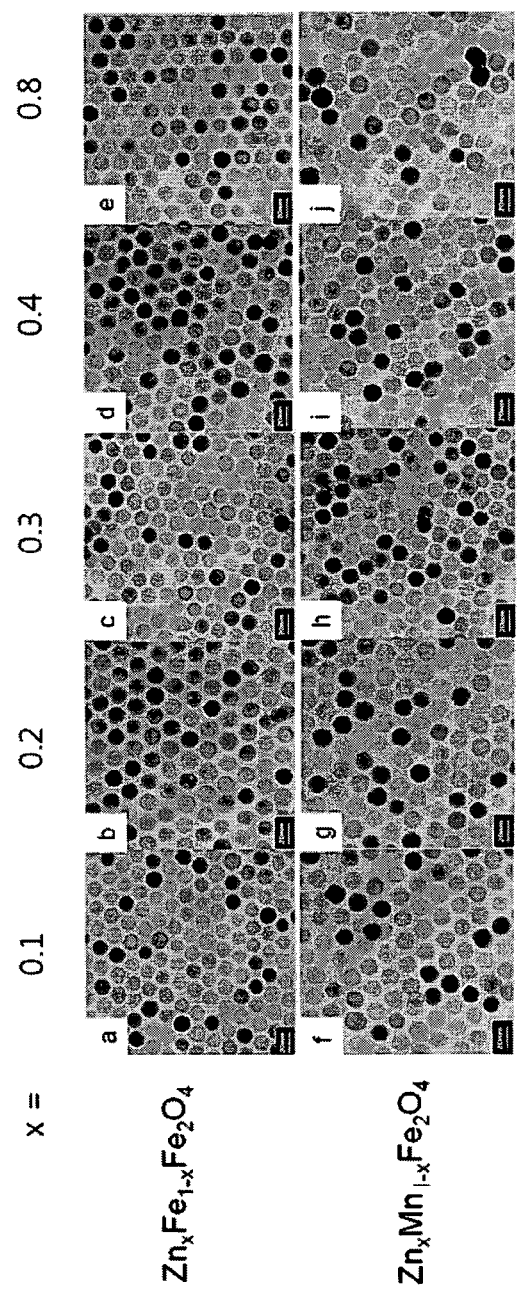
FIG. 2 is TEM images of zinc-containing ferrite nanomaterials synthesized. Panels a-e correspond to $Zn_xFe_{1-x}Fe_2O_4$ nanomaterials containing various zinc compositions (x=0.1, 0.2, 0.3, 0.4, and 0.8), and panels f-j correspond to $Zn_xMn_{1-x}Fe_2O_4$ nanomaterials containing various zinc compositions (x=0.1, 0.2, 0.3, 0.4, and 0.8). All nanomaterials with a size of 15 nm exhibit a homogeneous size distribution ($\delta < 10\%$).

All nanomaterials produced according to the above method have sphere shape with a homogeneous size, and the characteristics of nanomaterials were analyzed using TEM (Transmission Electron Microscopy) and EDS (Energy Dispersive X-ray Spectroscopy). TEM images of synthesized nanomaterials were shown in FIG. 1 and FIG. 2.

Example 2

Figure 3:
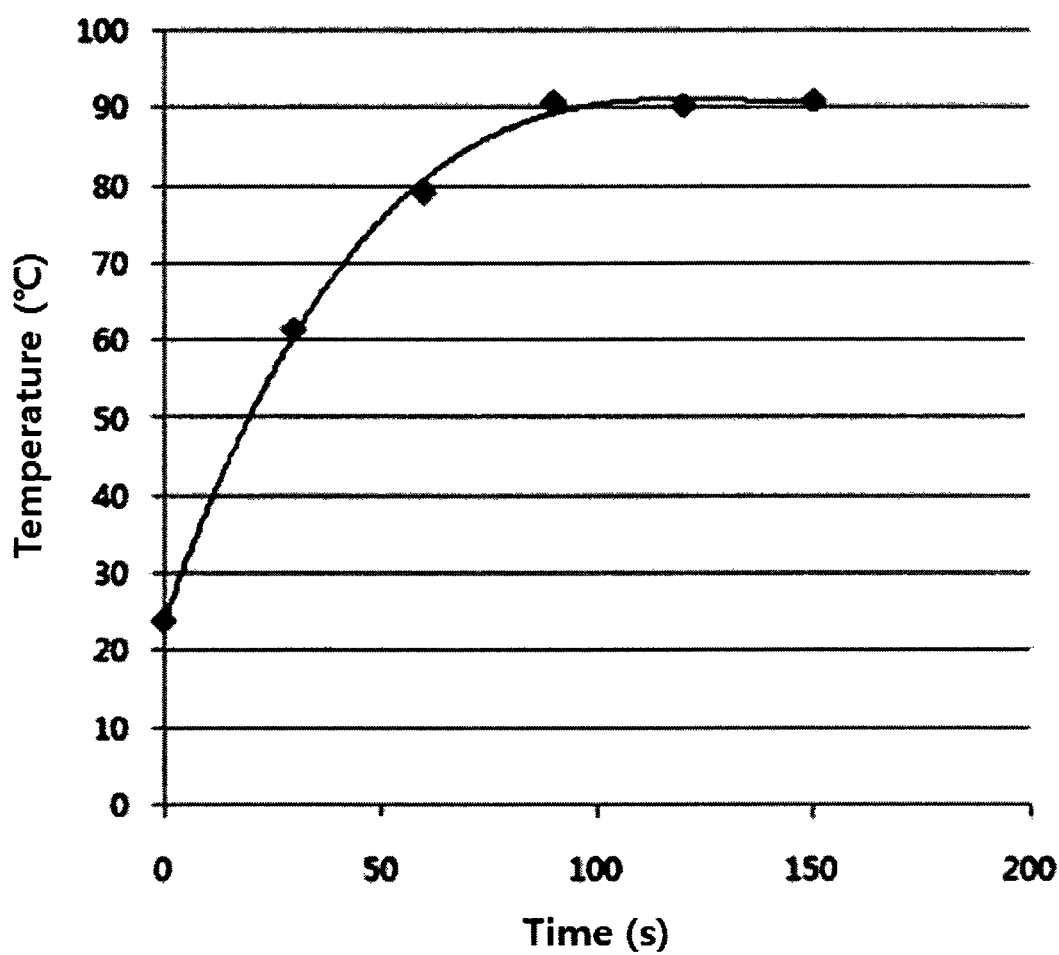
FIG. 3 is a graph representing a time-dependent temperature change of iron oxide nanomaterials under an alternative current magnetic field.

Comparison of Specific Loss Power Values of Magnetic Nanomaterials Having Different Sizes and Compositions To systematically compare the specific loss power of the magnetic nanomaterials with different size and composition, heat generated from the magnetic nanomaterials with different size and composition under the magnetic field of high frequency was measured under condition of the equal concentration. Based on the time-dependent temperature changes in coil with 5 cm diameter in 5 mg/mL solution under the alternative current magnetic field (frequency: 500 kHz, current: 35 A) (FIG. 3), the specific loss powers of the magnetic nanomaterials could be measured.

The specific loss powers are varied depending on size or composition of nanomaterials. In view of size of nanomaterials, the specific loss powers of $MnFe_2O_4$ or $NiFe_2O_4$ materials were likely to be increased according to increase in size. However, $Fe_3O_4$ is increased in a range of from 6 nm to 12 nm and is returned to be decreased in a range of above 12 nm. $CoFe_2O_4$ is decreased in a range of above 9 nm and is returned to be increased in 15 nm.

On the other hand, it was demonstrated that the specific loss powers of the nanomaterials are varied depending on the composition although their sizes are equal. For example, the specific loss power was changed according to addition of Zn to iron oxide and manganese ferrite with a size of 15 nm. Based on this result, it could be appreciated that the specific loss power is significantly affected depending on size and composition.

Figure 4:
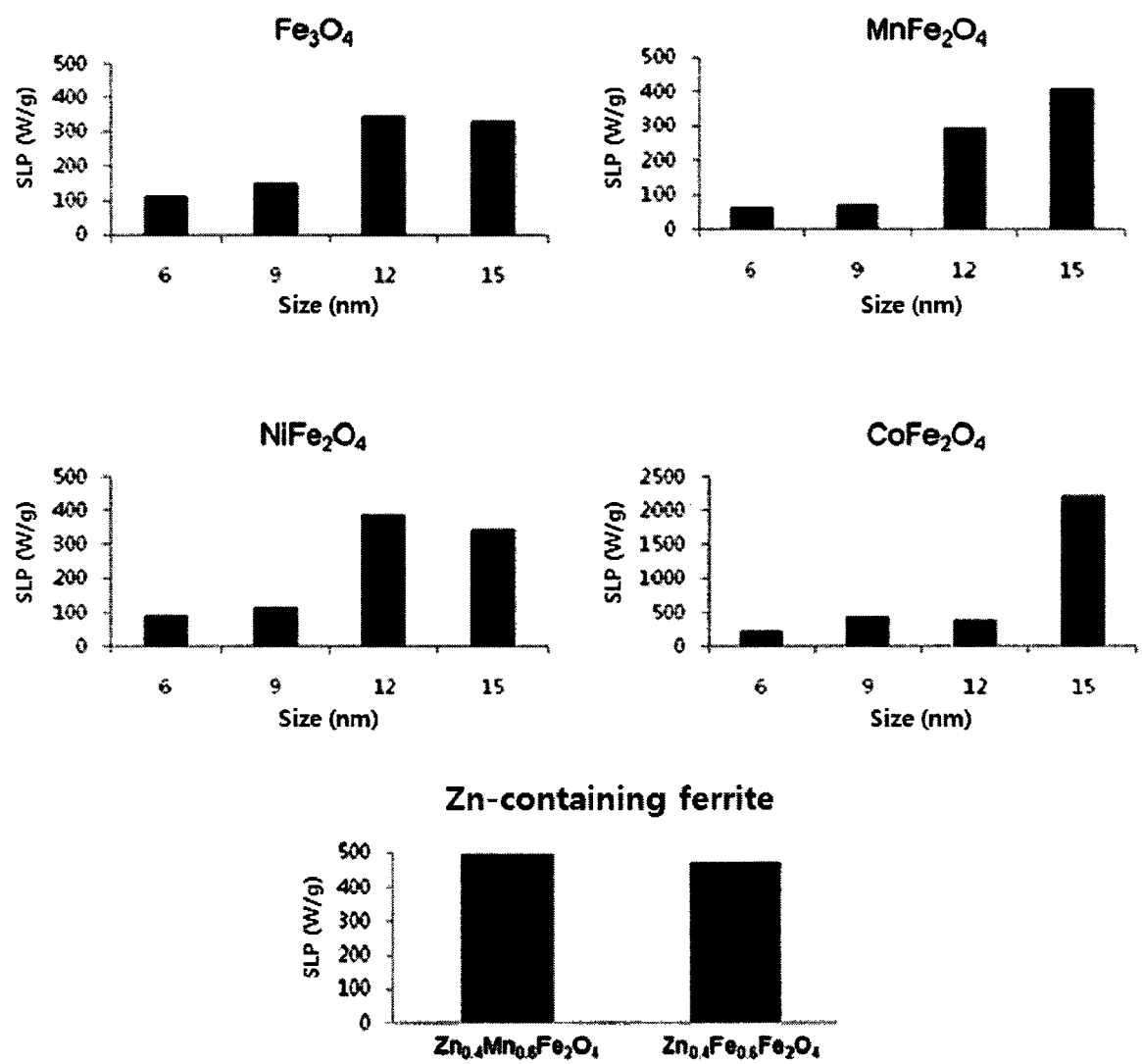
FIG. 4 represents histograms to show a size- or component-dependent specific loss power of magnetic nanomaterials ($MFe_2O_4$ (M=Mn, Fe, Ni, Co), $Zn_{0.4}Mn_{0.8}Fe_2O_4$, $Zn_{0.4}Fe_{0.8}Fe_2O_4$).

The specific loss power measured according to size and composition of nanomaterials was represented in FIG. 4.

Example 3

Preparation of Hetero-Structure Nanomaterials (Core-Shell Structure)

The hetero-structure nanomaterials containing the metal oxide nanomaterials used in the Examples were ferrite nanomaterials having total 15 nm-sized core-shell structure and were produced according to the methods described in Korean Pat. No. 10-0604975 and PCT/KR2004/003088 filed by the present inventors.

The first material was produced by the method represented in Example 1. The hetero-structure core-shell nanomaterials having 15 nm-sized core-shell structure could be yielded according to the following experimental method using 9 nm of first nanomaterials produced above. 9 nm-sized core-shell nanomaterials were added to $MCl_2$ ($M=Mn^{2+}$, $Fe^{2+}$, $Ni^{2+}$, $Co^{2+}$, and $Zn^{2+}$), $Fe(acac)_3$ as precursors of nanoparticles, and trioctylamine solvent (Aldrich, USA) containing 4 mmol oleic acid (Aldrich, USA) and 4 mmol oleylamine (Aldrich, USA) as capping molecules. The mixture was incubated at 200° C. under argon gas atmosphere and further reacted at 300° C. The nanomaterials produced using a seed-mediated method have 15 nm-sized core-shell structure. The separation procedure was performed according to the method as same as synthesis of core nanomaterials.

Figure 5:
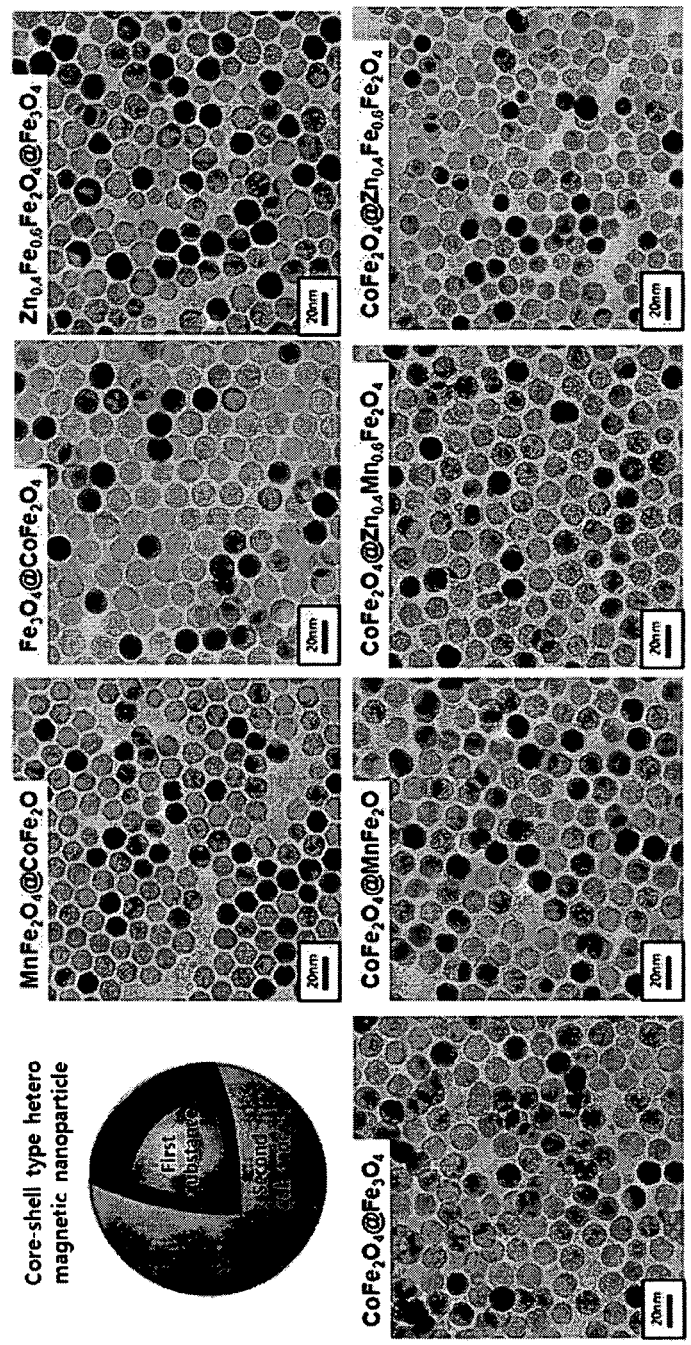
FIG. 5 is TEM images of core-shell typed hetero magnetic nanomaterials.

The core-shell type hetero-structure nanomaterials could be varied depending on compositions of the first material used and metal precursors selected. For example, $CoFe_2O_4@Fe_3O_4$, $CoFe_2O_4@MnFe_2O_4$, $CoFe_2O_4@Zn_{0.4}Fe_{0.6}Fe_2O_4$, $CoFe_2O_4@Zn_{0.4}Mn_{0.6}Fe_2O_4$, $MnFe_2O_4@CoFe_2O_4$, $Fe_3O_4@CoFe_2O_4$ and $Fe_3O_4@MnFe_2O_4$ could be effectively yielded. The synthetic nanomaterials are monodispersed sphere and their characteristics were analyzed using TEM and EDS. TEM images of synthesized nanomaterials were shown in FIG. 5.

Example 4

Analyses of Specific Loss Power Values of Hetero-Structure Nanomaterials

Figure 6:
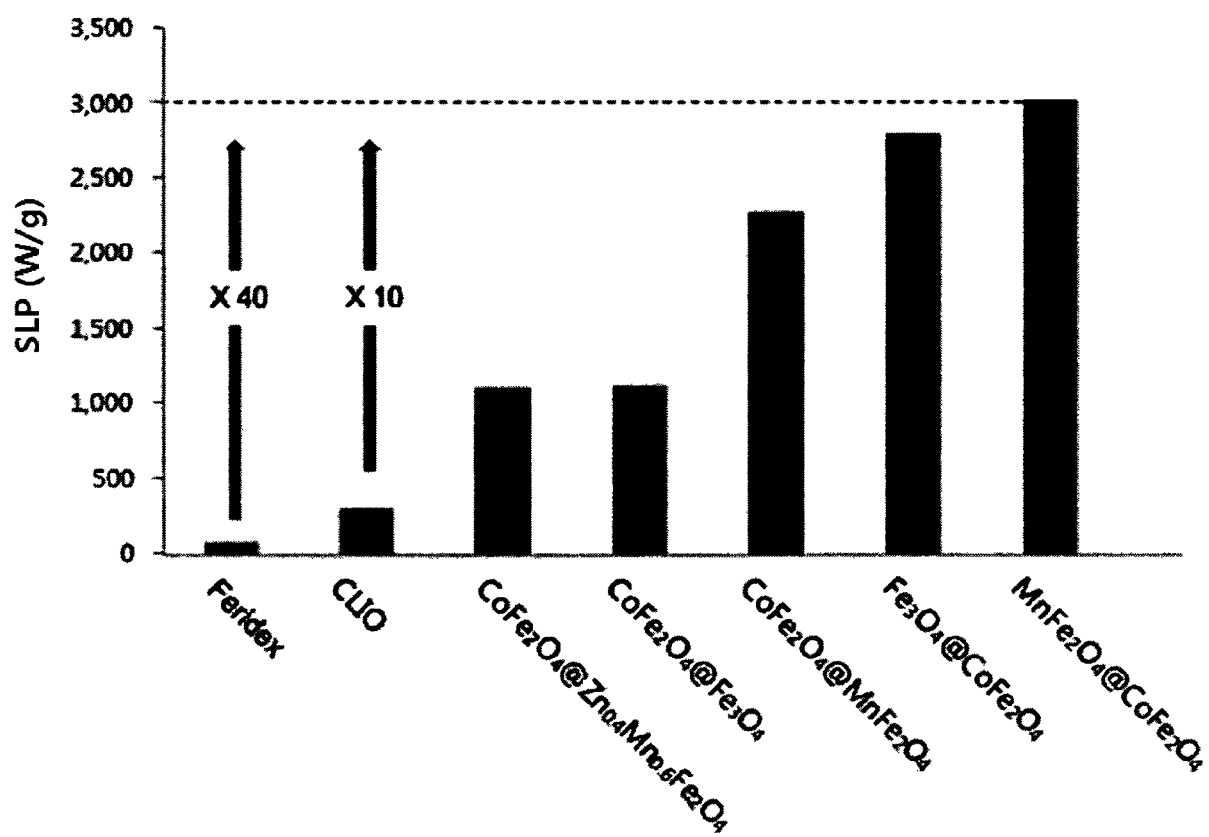
FIG. 6 represents a histogram to show the specific loss power of the core-shell typed hetero magnetic nanomaterials synthesized. It could be understood that the core-shell typed hetero magnetic nanomaterials have much more remarkable specific loss power than commercially accessible nanomaterials, Feridex and CLIO.

The specific loss power of the nanomaterials produced in Example 3 was measured according to the method as same as Example 2. The specific loss powers of various nanomaterials containing 15 nm-sized $CoFe_2O_4@Fe_3O_4$, $CoFe_2O_4@MnFe_2O_4$, $MnFe_2O_4@CoFe_2O_4$, $Fe_3O_4@CoFe_2O_4$, $CoFe_2O_4@Zn_{0.4}Fe_{0.6}Fe_2O_4$ and $CoFe_2O_4@Zn_{0.4}Mn_{0.6}Fe_2O_4$ were measured and compared with those of magnetic nanomaterials (Feridex or CLIO) commercialized in common. Comparative data between the specific loss powers of core-shell nanomaterials produced and other materials are represented in FIG. 6. The core-shell nanomaterials produced exhibit the marked specific loss power and in particular, the specific loss power of $MnFe_2O_4@CoFe_2O_4$ is increased 40-fold and 10-fold higher than that of commercial nanomaterials, Feridex and CLIO, respectively.

Example 5

Evaluation of Inducing Cancer Cell Apoptosis

The nanomaterials having enhanced specific loss power can be applied in various fields. The nanomaterials having enhanced specific loss power may be applied in various fields. As a representative example, the nanomaterials are very efficiently used in cancer cell apoptosis. Based on the fact that cancer cells are likely to be killed around 40-50° C. unlikely normal cells, nanomaterials having enhanced specific loss power become promising as cancer hyperthermia agents by inducing cancer cell apoptosis because even a very low dose of nanomaterials generates higher heat. To verify the hyperthermic effect, the equal amounts of commercially purchasable Feridex and the nanomaterials of the present invention having remarked specific loss power were incubated with cancer cells and then kept to stand under magnetic field with high frequency. As a result, the novel nanomaterials ($MnFe_2O_4@CoFe_2O_4$) having enhanced specific loss power showed much more remarkable cancer cell apoptosis than a commercially accessible nanomaterials (Feridex).

Figure 7:
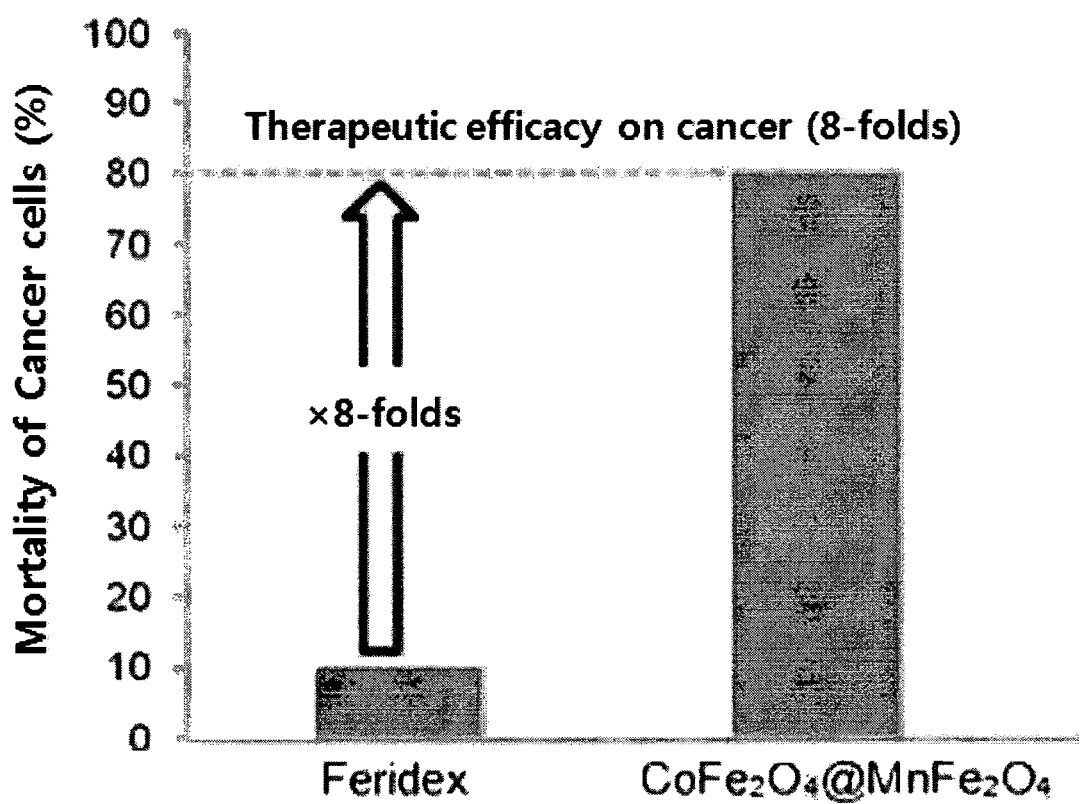
FIG. 7 is comparative results for cancer hyperthermic efficacies (cancer cell apoptosis) of the core-shell typed hetero magnetic nanomaterial and Feridex. It is revealed that the cancer treatment efficacy of the core-shell typed hetero magnetic nanomaterial ($MnFe_2O_4@CoFe_2O_4$) is over 8-fold higher than that of commercially purchasable nonmaterial, Feridex.

The hyperthermic efficacy on cancer cells of $MnFe_2O_4@CoFe_2O_4$ among core-shell typed nanomaterials obtained in Example 3 was evaluated. The nanomaterials produced in Example 3 were solubilized in water according to the methods described in Korean Pat. No. 0604976, No. 0652251, PCT/KR2004/003088, Korean Pat. No. 0713745 and PCT/KR2007/001001 filed by the present inventors. Five mg of $MnFe_2O_4@CoFe_2O_4$ was added to a dimethylsulfoxide (DMSO) solution containing 20 mg of dimethylsuccinic acid (DMSA) and reacted for 12 hrs. Afterwards, the nanomaterial was precipitated by centrifugation, dried and titrated using 1 M NaOH, followed by dissolving in water. 0.5 mg/mL of $MnFe_2O_4@CoFe_2O_4$ nanomaterial was incubated with $1\times10^7$ of HeLa cells in 1 mL cell culture media and then alternative current magnetic field (frequency: 500 kHz, current: 35 A) was introduced on them for 5 min using coils with 5 cm diameter. Cell mortality was measured in accordance with a CCK-8 assay. Surprisingly, the $MnFe_2O_4@CoFe_2O_4$ nanomaterial was analyzed to induce cell viability of no less than 80% for HeLa cells, while Feridex to cell viability of 10% under the same condition. Therefore, it could be appreciated that the cancer hyperthermic efficacy of $MnFe_2O_4@CoFe_2O_4$ nanomaterial is about 8-fold higher than that of Feridex. FIG. 7 represents comparative data on cancer cell killing induced by the present nanomaterial and the commercially accessible nanomaterial (Feridex).

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A composition comprising a hetero-structure nanomaterial which comprises (a) a first material comprising $MnFe_2O_4$; and (b) a second material comprising $CoFe_2O_4$; wherein the first material is enclosed in the second material.

2. The composition according to claim 1, wherein the hetero-structure is (i) a zero-dimensional structure selected from the group consisting of a core-shell and a multi-core shell structure; (ii) a one-dimensional structure selected from the group consisting of a barcode, a core-shell coaxial rod structure, and a multi-core shell coaxial rod structure; (iii) a two-dimensional structure comprising a multi-component sheet structure; or (iv) a three-dimensional structure selected from the group consisting of a dumbbell and a multi-pod structure.

3. The composition according to claim 1, wherein the hetero-structure has the zero-dimensional structure comprising the core-shell or multi-core shell structure.

4. A method for body imaging, said method comprising administering to a subject the composition of claim 1.

5. A method for body imaging, said method comprising administering to a subject the composition of claim 2.

6. A method for body imaging, said method comprising administering to a subject the composition of claim 3.

* * * * *